United States Patent [19]

Kato et al.

[11] 3,994,593
[45] Nov. 30, 1976

[54] APPARATUS FOR AUTOMATIC QUANTITATIVE ANALYSIS OF BLOOD SERUM SPECIMENS BY CATAPHORETIC PROCESS

[75] Inventors: Yutaka Kato, Tama; Teruo Ouchi, Hachioji, both of Japan

[73] Assignee: Olympus Optical Co., Ltd., Tokyo, Japan

[22] Filed: Oct. 2, 1975

[21] Appl. No.: 618,912

[30] Foreign Application Priority Data

Oct. 7, 1974 Japan............... 49-120228[U]

[52] U.S. Cl............................. 356/203; 356/36; 356/39
[51] Int. Cl.[2]........................................ G01N 21/06
[58] Field of Search ............. 356/36, 39, 201, 202, 356/203

[56] References Cited
UNITED STATES PATENTS

| | | | |
|---|---|---|---|
| 3,388,652 | 6/1968 | Parrent | 356/36 |
| 3,902,971 | 9/1975 | Fletcher | 356/36 |
| 3,924,947 | 12/1975 | Hogg | 356/36 |

FOREIGN PATENTS OR APPLICATIONS

| | | | |
|---|---|---|---|
| 1,367,706 | 9/1974 | United Kingdom | 356/36 |

*Primary Examiner*—John K. Corbin
*Assistant Examiner*—Richard A. Rosenberger

[57] ABSTRACT

An apparatus for automatic quantitative analysis of specimens of a blood serum by a cataphoretic process comprises a supply of a clearing liquid which is supplied to a film on which a plurality of specimens are disposed at a constant pitch, light source means for projecting light onto the film which has been made clear by the application of the clearing liquid thereto, measuring means including a photoelectric transducer element which receives and determines the light which has transmitted through the film, feed means for intermittently feeding the film so as to locate it at a measuring port which is positioned between the light source means and the photoelectric transducer element, and scan drive means for displacing the light source means and the photoelectric transducer means crosswise of the film to scan a particular one of the specimens which is positioned at the measuring port each time the film comes to a stop. In this manner, the film carrying the specimens is made clear by the clearing liquid, and a quantitative analysis is made by scanning the individual specimens by the photoelectric transducer element in the course of the intermittent feed of the film, all in an automatic manner.

9 Claims, 8 Drawing Figures

APPARATUS FOR AUTOMATIC QUANTITATIVE ANALYSIS OF BLOOD SERUM SPECIMENS BY CATAPHORETIC PROCESS

BACKGROUND OF THE INVENTION

The invention relates to an apparatus for automatic quantitative analysis, by cataphoretic process, of the amount of protein, for example, which is contained in a blood serum.

A specimen film is obtained by applying a blood serum on a cellulose acetate film at a given pitch, disposing a pair of electrodes on the opposite sides of the serum applied, energizing the electrodes to fractionate the serum components, which are then dyed, followed by decolorizing unnecessary portions and drying, thus producing a specimen film carrying a plurality of fractionated patterns of the blood serum distributed lengthwise thereof at a given pitch and each extending crosswise thereof. Subsequently, the specimen film is made clear by applying a clearing liquid such as fluid paraffin or decalin to the film or immersing the film into such a clearing liquid, and the film is disposed in a densitometer to provide a quantitative analysis by determining the density of the fractionated patterns of the individual specimens.

The usual practice has been to employ a manual operation for making the specimen film clear and for all other operations required for the determination, resulting in a very inefficient operation. In particular, a commerically available densitometer permits the determination of only up to eight specimens at one time, so that the specimen film had to be cut into sections, each including eight specimens, which added further difficulty to the overall operation.

SUMMARY OF THE INVENTION

It is an object of the invention to provide an apparatus for quantitative analysis, by cataphoretic process, of the specimens comprising a blood serum and which are carried on a film wherein the step of making the specimen film clear and the step of measuring the cleared specimen film are fully automated.

In accordance with the invention, the specimen film is intermittently fed while treating it with the clearing liquid, and then the individual specimens are successively located at a measuring port which is positioned between a light source and a photoelectric transducer element. During the time the specimen film remains stationary at the measuring port, the light source and the photoelectric transducer element are displaced crosswise of the film to scan a particular specimen. In this manner, the combination of the intermittent feed means and the scan drive means which displaces the light source and the photoelectric transducer element crosswise of the film during the time it remains stationary permits a complete automation of the overall apparatus, enabling an efficient processing of an elongate specimen film.

DETAILED DESCRIPTION OF PREFERRED EMBODIMENTS

Figure 1:
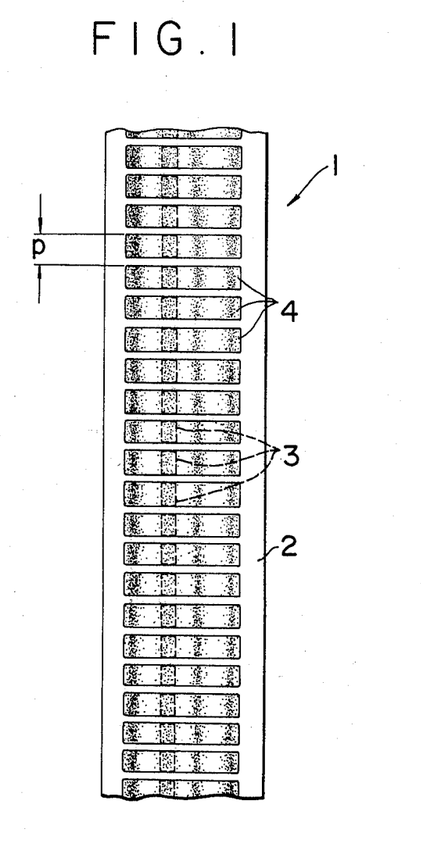
FIG. 1 is a top view of one example of a specimen film.

Referring to FIG. 1, there is shown one example of a specimen film 1. The specimen film 1 is generally produced by a series of steps as mentioned below.

Figure 2:
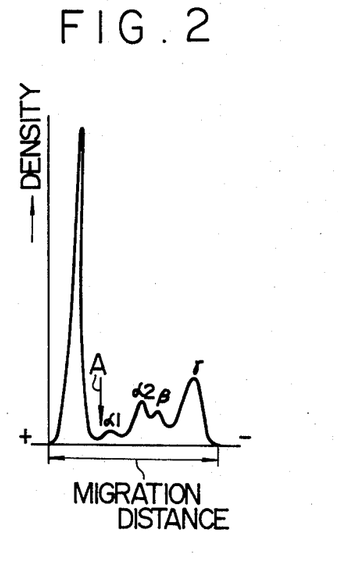
FIG. 2 graphically shows an exemplary density distribution of a typical fractionated pattern of the specimen.

1. A carrier film 2 which comprises cellulose acetate is wetted with Veronal-Veronal soda buffer solution.
2. A blood serum 3 is applied to the carrier film 2 at a given pitch $p$.
3. A pair of positive and negative electrodes are disposed on the opposite sides of the carrier film, as viewed crosswise thereof, and energized to effect a cataphoresis of the serum 3, which is caused to migrate to produce a fractionated pattern. The direction and the distance of migration of various components contained in the blood serum 3 vary depending on their polarity, and FIG. 2 shows a typical distribution. In FIG. 2, the abscissa represents the distance of migration along the width and the ordinate the density, indicating a density distribution of fractionated components. The peak which is located leftmost represents the density of albumin, which is formed toward the positive electrode relative to the position A where the blood serum is applied. Viewing from left to right, successive peaks designated by characters $\alpha_1$, $\alpha_2$, $\beta$ and $\gamma$ represent the density of corresponding globulin components, and are formed toward the negative electrode.
4. The carrier film 2 having the fractionated pattern obtained by the cataphoresis of the serum components is dyed and then decolorized, whereby only the fractionated pattern remains colorized to provide a specimen 4 (see FIG. 1).
5. The carrier film 2 having a number of specimens 4 formed thereon is dried to provide a specimen film 1.

The apparatus according to the invention is directed to making the specimen film 1 thus obtained clear by treating it with a clearing liquid and determining the density of the fractionated pattern of respective specimens on the specimen film 1 as by a colorimeter or a densitometer. One embodiment of such apparatus is shown in FIG. 3.

Figure 3:
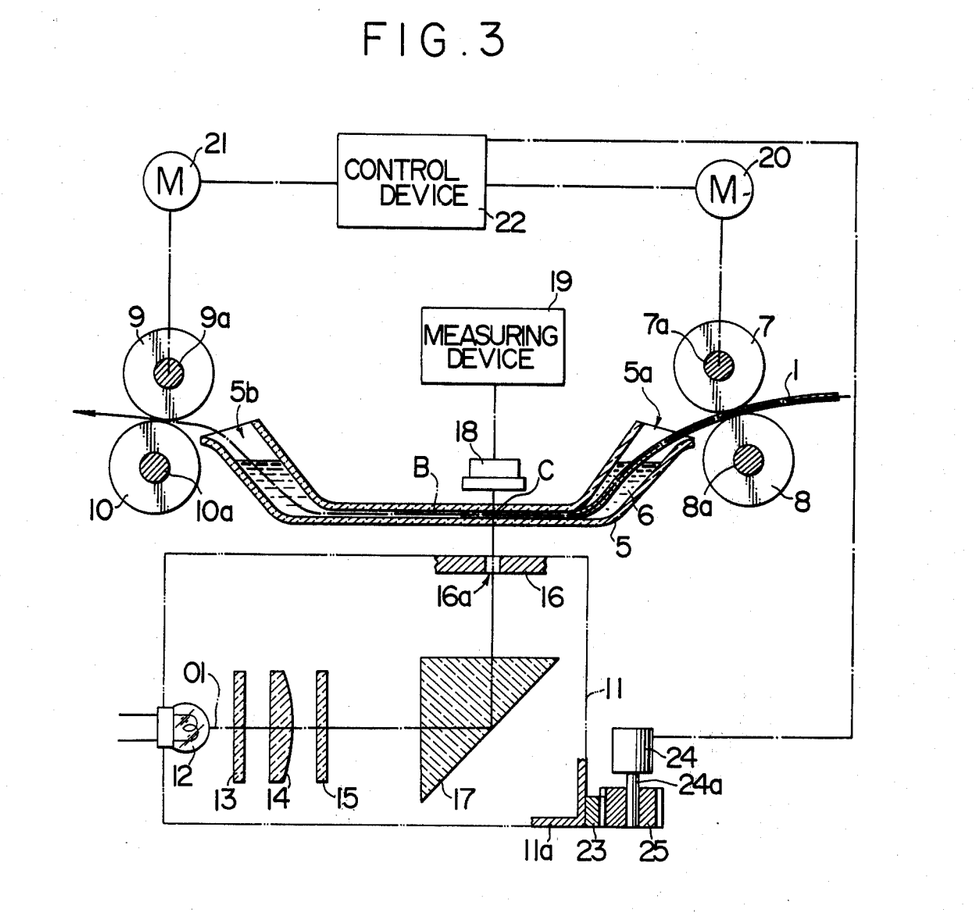
FIG. 3 is a side elevation of an apparatus for automatic quantitative analysis of specimens by cataphoretic process which is constructed in accordance with one embodiment of the invention.

Referring to FIG. 3, the apparatus shown includes a transparent vessel 5 formed of acrylic resin or glass and which contains a quantity of clearing liquid 6 such as fluid paraffin, decalin or the like. The vessel 5 shown is in the form of a hollow cylinder with the central portion being recessed and flattened. At its right-hand end, the vessel is provided with an inlet 5a for the specimen film 1, and is also provided with an outlet 5b at its left-hand end. A pair of mating feed rollers 7, 8 are disposed adjacent to the inlet 5a and are carried by shafts 7a, 8a. Similarly, a pair of mating delivery rollers 9, 10 are disposed adjacent to the outlet 5b and are carried by shafts 9a, 10a. The feed rollers 7, 8, the internal passage of the vessel 5 and the delivery rollers 9, 10 define in combination a feed path B for the specimen film 1.

A light source unit 11 is disposed on one side of the vessel 5, or below it as illustrated in the drawing, and comprises a lamp 12, an optical path $O_1$ for the light emanating from the lamp 12 and on which an infrared ray absorptive filter 13, a condenser lens 14 and a colorimetric filter 15 are disposed, and a prism 17 which diverts the light from the optical path $O_1$ toward a slit 16a formed in a slit member 16. The slit member 16 is located so as to emit an illuminating light through the slit 16a in a perpendicular direction onto the central flat portion of the vessel 5. The slit 16a also serves as a diaphragm and preferably has a width less than 1.0 mm. On the opposite side of the vessel 5 from the light source unit 11, or above the vessel 5, is disposed a photoelectric transducer element 18 which receives the light emanating from the slit 16a and transmitted through the vessel 5 and the specimen film 1. A measuring port C is defined at the intersection of the optical path $O_1$ of the illuminating light and the feed path B of the specimen film 1. The output terminals of the photoelectric transducer element 18 are connected with a measuring device 19 such as a colorimeter or densitometer.

The shafts 7a, 9a of the rollers 7, 9 are operatively connected with a pair of motors 20, 21, which are intermittently driven in mutual synchronism under the control of a control device 22, thereby causing the specimen film 1 to be fed by an increment corresponding to the pitch p of the specimens 4 located on the film 1 (see FIG. 1) by means of the feed rollers 7, 8 and the delivery rollers 9, 10. The motors 20, 21 may each comprise a stepping motor, or alternatively a single motor may be used to drive the both rollers 7, 9.

The light source unit 11 includes a housing 11a, which is formed with a rack 23 meshing with a pinion 25 fixedly mounted on an output shaft 24a of a motor 24. The motor 24 is under the control of the control device 22 so as to operate during the time the motors 20, 21 remain stationary, thus driving the rack 23 through the pinion 25. The light source unit 11 and the transducer element 18 are integral structurally, so that when the rack 23 is driven, they are displaced crosswise of the specimen film 1 at the measuring port C, thus scanning a particular one of the specimens.

In operation, the specimen film 1 is loaded by the feed rollers 7, 8 into the vessel 5 to a position such that the foremost specimen 4 is located at the measuring port C. At this time, the light source unit 11 and the transducer element 18 are laterally spaced from the specimen film 1, and as the motor 24 is operated, the unit 11 and the transducer element 18 are displaced across the specimen film 1, thus scanning the foremost specimen 4. During this scanning of the specimen 4, the output of the transducer element 18 varies in accordance with the amount of incident light transmitted through the respective areas of the fractionated pattern and which also varies in correspondence with the density of such areas. In this manner, the density of the fractionated pattern is determined by the measuring device 19. Where a colorimetric quantitative analysis of the components is desired, the illuminating light from the light source unit 11 has a wavelength on the order of 490 to 600 m$\mu$.

Upon termination of the scanning of the foremost specimen 4, the motor 24 is driven in the opposite direction, whereby the light source unit 11 and the transducer element 18 are returned to their initial position. During such returning movement, the lamp 12 is extinguished. When the light source unit 11 and the transducer element 18 have returned to their initial position, the motor 24 is deenergized and instead the motors 20, 21 are energized, rotating the feed rollers 7, 8 and the delivery rollers 9, 10 in order to feed the specimen film 1 by one pitch p (see FIG. 1). After feeding the film 1 by one pitch, the motors 20, 21 are deenergized again, and a second specimen 4 which is now located at the measuring port C is scanned in the similar manner as mentioned above in connection with the foremost specimen 4. Such operation is repeated to conduct the measurement of the individual specimens 4 carried by the specimen film 1 in an automatic and successive manner.

Figure 4:
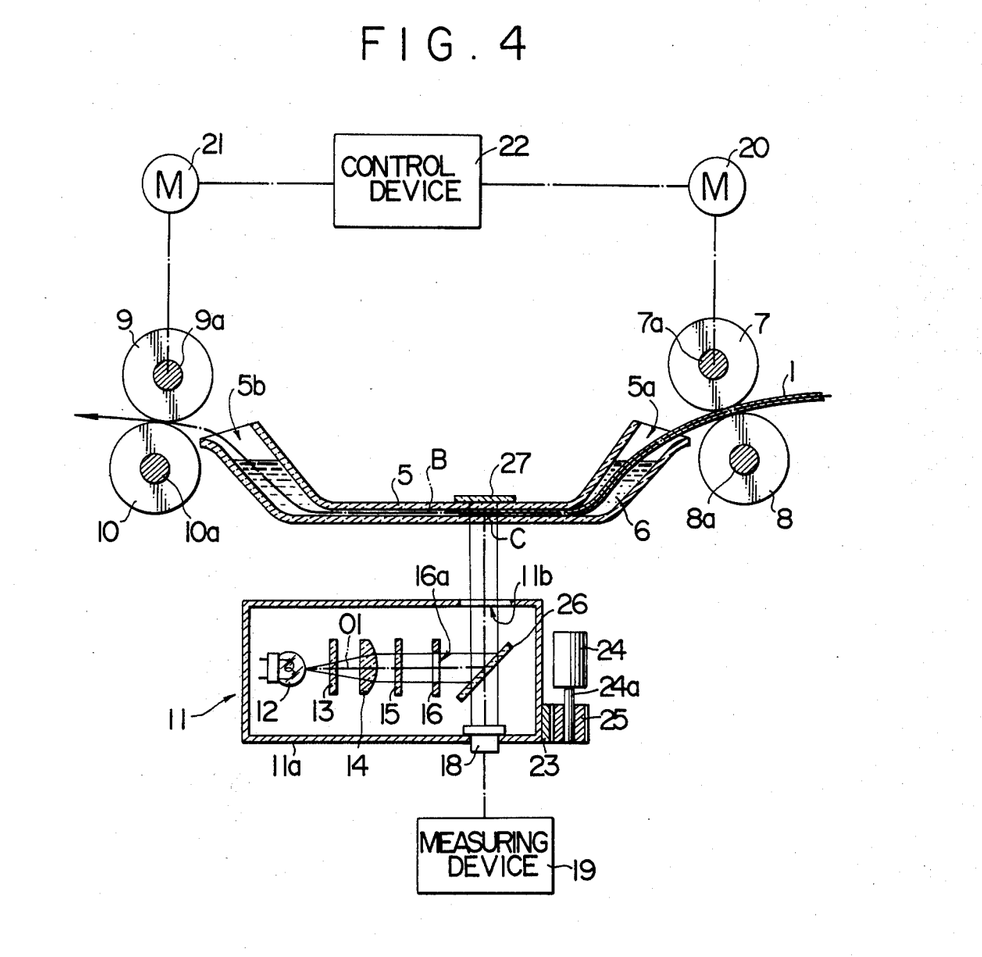
FIG. 4 is a side elevation of another embodiment of the invention.

FIG. 4 shows another embodiment of the invention wherein a reflecting mirror is used to cause the illuminating light to be transmitted through the specimen film twice before being received by the photoelectric transducer element. Parts in FIG. 4 which are similar in function to those of FIG. 3 are designated by like reference characters and will not be specifically described. In the arrangement of FIG. 4, the slit member 16 is disposed in alignment with and to the right-hand side of the filter 15, and a half mirror 26 is disposed to the right of the slit member 16 at an angle of inclination with respect to the optical axis $O_1$. The half mirror 26 is adapted to direct a portion of the illuminating light in the upward direction through an opening 11b formed in the housing 11a. A reflecting mirror 27 is disposed against the upper wall of the vessel 5 in the region of the measuring port C for reflecting the light which has transmitted through the vessel 5 and the specimen film 1 back to the half mirror 26 by transmission through the vessel 5 and the specimen film 1 again. The photoelectric transducer element 18 is secured to the housing 11a at a position below the half mirror 26 for receiving a portion of the light which has twice transmitted through the vessel 5 and the specimen film 1, subsequent its transmission through the half mirror 26. The use of the reflecting mirror 27 to cause the illuminating light to be transmitted through the specimen film 1 twice improves the accuracy of measurement and also permits the apparatus to be constructed as a compact unit.

Referring to FIGS. 5 to 8, a further embodiment of the invention will be described. Initially referring to FIGS. 5 and 6, an apparatus 101 for quantitative analysis comprises a pair of sideplates 101a, 101b which are firmly connected together by a pair of interconnecting rods 107, 108 and a pair of guide rods 138, 139. A liquid vessel 102 having a pair of deep recesses 102a, 102b adjacent to its opposite ends is disposed in the upper region of the both sideplates 101a, 101b. One of the recesses, 102a, receives a supply of clearing liquid 103a similar to the clearing liquid 6 mentioned above which is to be supplied to a specimen film 110, while the other recess 102b receives the same clearing liquid 103b which drips from the specimen film 110. Centrally, the vessel 102 is also formed with a shallow recess 102c in which a transparent glass plate 104a is embedded. In the region of the glass plate 104a, a retaining plate 105 is placed thereon and has a transparent glass plate 104b fitted therein at a position opposite to the glass plate 104a. The glass plates 104a, 104b maintain a small clearance therebetween and form part of a feed path 110A for the specimen film 110, which is constructed in the similar manner as the specimen film 1 mentioned previously.

Figure 5:
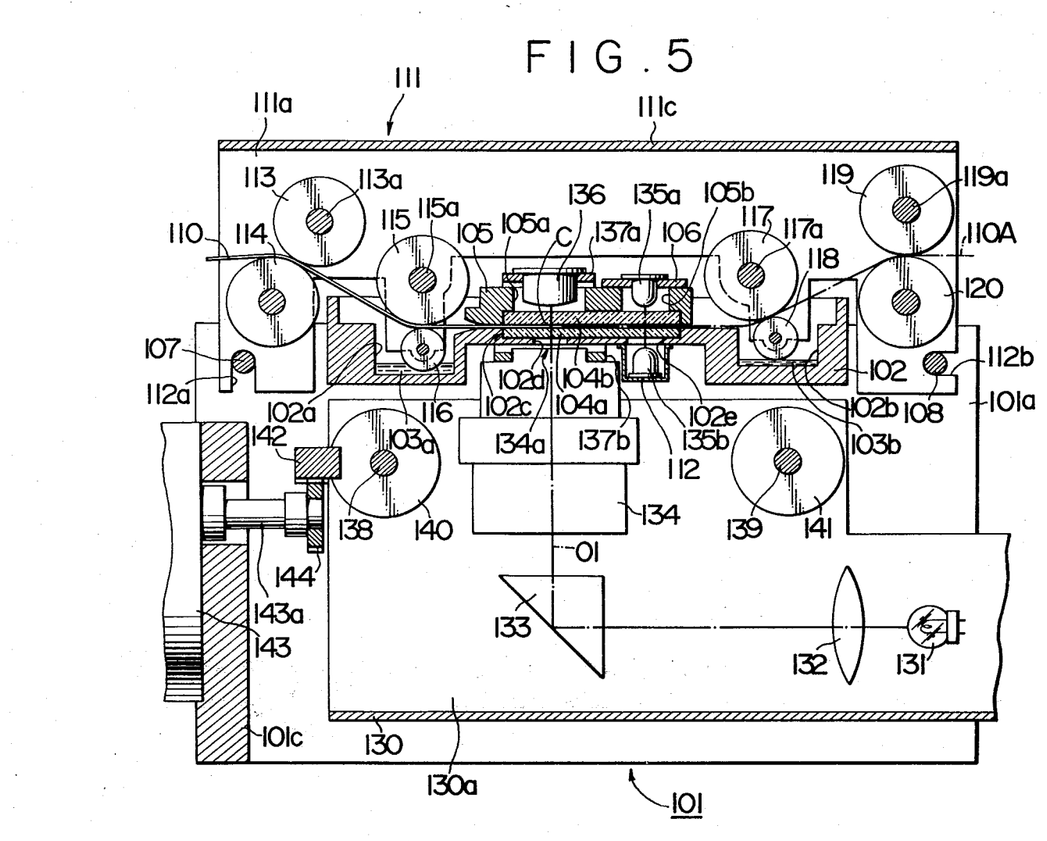
FIG. 5 is a side elevation of a further embodiment of the invention.
Figure 6:
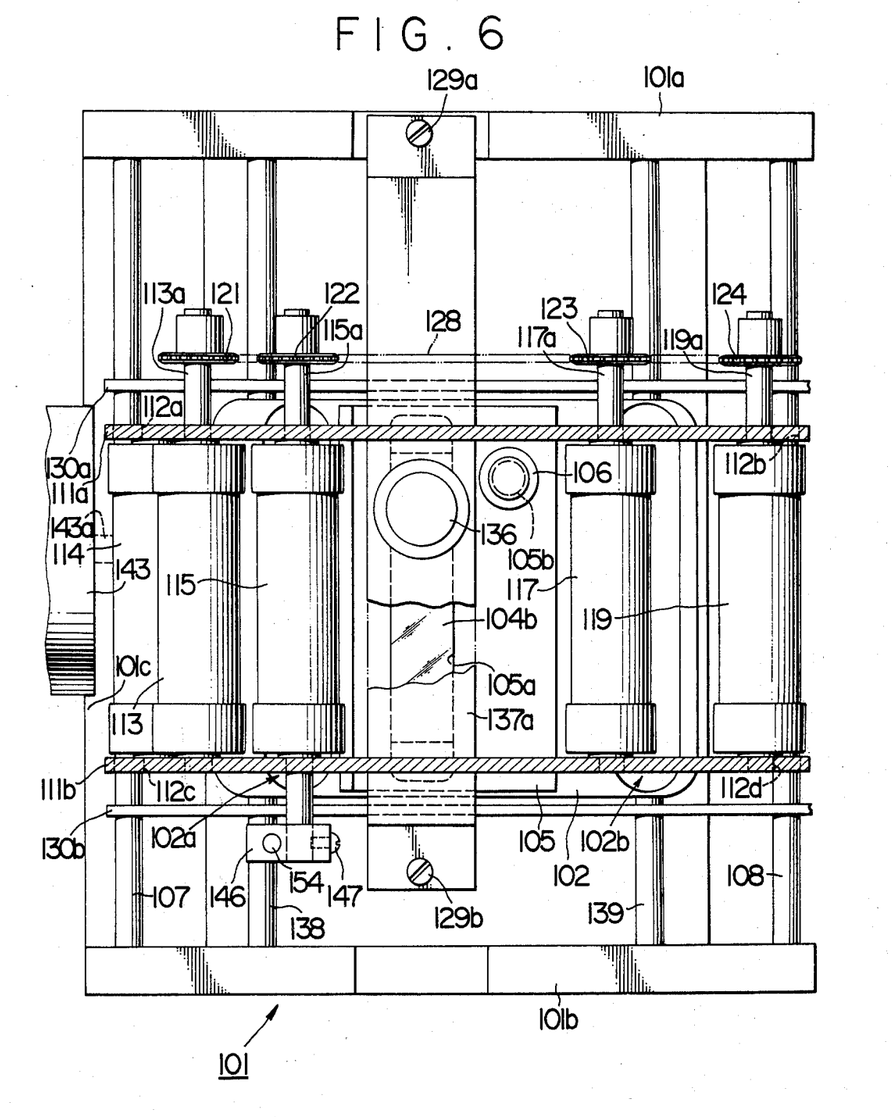
FIG. 6 is a top view of the apparatus shown in FIG. 5.

A roller support box 111 is mounted on the pair of connecting rods 107, 108, by engaging notches 112a, 112b, 112c, 112d formed in the lower parts of the opposite ends of its sidewalls 111a, 111b with these rods. Four pairs of mating feed rollers 113, 114; 115, 116; 117, 118; and 119, 120 are rotatably mounted on the sidewalls 111a, 111b of the box 111, the pair of rollers 115, 116 and the pair of rollers 117, 118 being located above the recesses 102a and 102b, respectively, of the liquid vessel 102, and the pair of rollers 113, 114 and the pair of rollers 119, 120 being located outwardly of the first mentioned pairs of rollers. The respective rollers define the feed path 110A for the specimen film 110 in conjunction with the glass plates 104a, 104b, and the roller 116 is partially immersed into the clearing liquid 103a contained in the recess 102a. The rollers 113, 115, 117 and 119 are mounted on shafts 113a, 115a, 117a and 119a, respectively, one end of which fixedly carries gears 121, 122, 123 and 124, respectively, as shown in FIG. 6. A chain 128 extends around these gears and also around a gear 127 (see FIG. 7) which is fixedly mounted on the shaft 125a of a continuous feed motor 125 which is in turn fixedly mounted on the top 111c of the box 111 by means of a support member 126.

A box 130 for supporting the light source unit is disposed below the liquid vessel 102 by slidably engaging the guide rods 138, 139 with a pair of mounting discs 140, 141 which are fitted into the opposite sidewalls 130a, 130b of the box 130. As shown in FIG. 5, the box 130 houses a lamp 131, a condenser lens 132, a prism 133 and a group of condenser lenses 134. Specifically, an illuminating light emanating from the lamp 131 is directed along an optical path $O_1$ defined by these optical members and projected upwardly through an exit pupil 134a for transmission through an elongate slot 102d which is formed in the lower sidewall of the vessel 102 in the region below the glass plate 104a, and then through the glass plate 104a, the specimen film 110 and the glass plate 104b. It is to be noted that as viewed in FIG. 5, the slot 102d is elongate in the direction perpendicular to the plane of the drawing while it extends in the vertical direction as viewed in FIG. 6. An elongate slot 105a extending in the same direction as the slot 102d is formed in the portion of the retaining plate 105 which is located above the glass plate 104b, and receives a light receiving portion of a photoelectric transducer element which is supported by a support plate 137a. A measuring port C is defined at the intersection of the optical path $O_1$ of the illuminating light and the feed path 110A of the specimen film 110. A slot 105b is formed in a portion of the retaining plate 105 which is located in the upper, right-hand portion thereof, as viewed in FIG. 6 and receives a light receiving portion of a photoelectric transducer element 135a which is secured to the retaining plate 105 by means of a mounting plate 106. In a region of the liquid vessel 102 which is located below the transducer element 135a, there is formed a slot 102e as shown in FIG. 5, and a light emitting diode 135b is mounted on the liquid vessel 102 by means of a mounting member 112 so as to be located below the slot 102e. The combination of the transducer element 135a and the light emitting diode 135b is effective to detect a position mark (not shown) on the specimen film 110 for controlling the operation of various parts of the apparatus.

As shown in FIG. 6, the support plate 137a for the transducer element 136 extends below the lower end of the sidewalls 111a, 111b of the roller support box 111, and then its opposite ends are bent laterally in opposite directions, where it is secured to a bracket 137b (see FIG. 5) which is secured to the top of the condenser lens assembly 134, by means of set screws 129a, 129b (see FIG. 6).

The disc 140 which is secured to the box 130 supporting the light source unit and which is slidably mounted on the guide rod 138 is integrally formed with a rack 142, which meshes with a pinion 144 fixedly mounted on the output shaft 143a of a scan motor 143. The scan motor 143 is secured to the support plate 101c which is secured across the both sideplates 101a, 101b of the apparatus 101. When the scan motor 143 is energized, the pinion 144 is rotated to drive the rack 142, which in turn causes the box 130 to be axially displaced along the guide rods 138, 139. A displacement of the box 130 in this direction also causes a displacement of the transducer element 136 in the same direction, thus scanning the specimen film 110.

Figure 7:
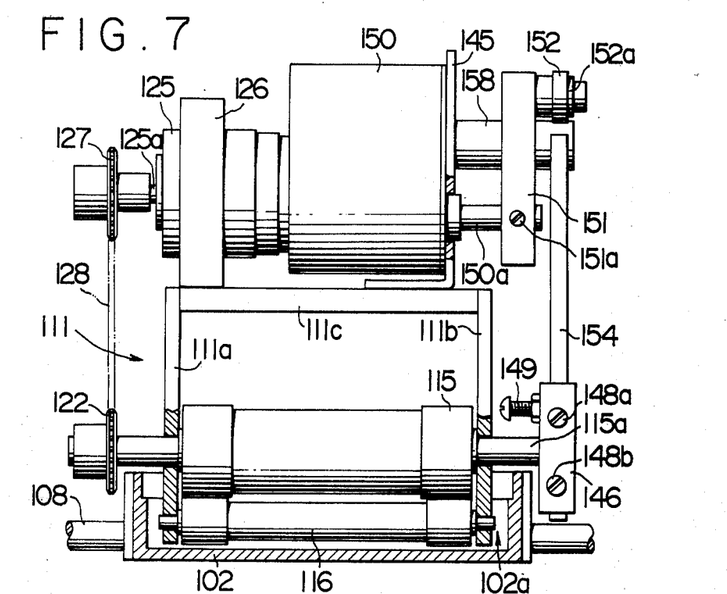
FIG. 7 is a fragmentary front view of the apparatus shown in FIG. 5.
Figure 8:
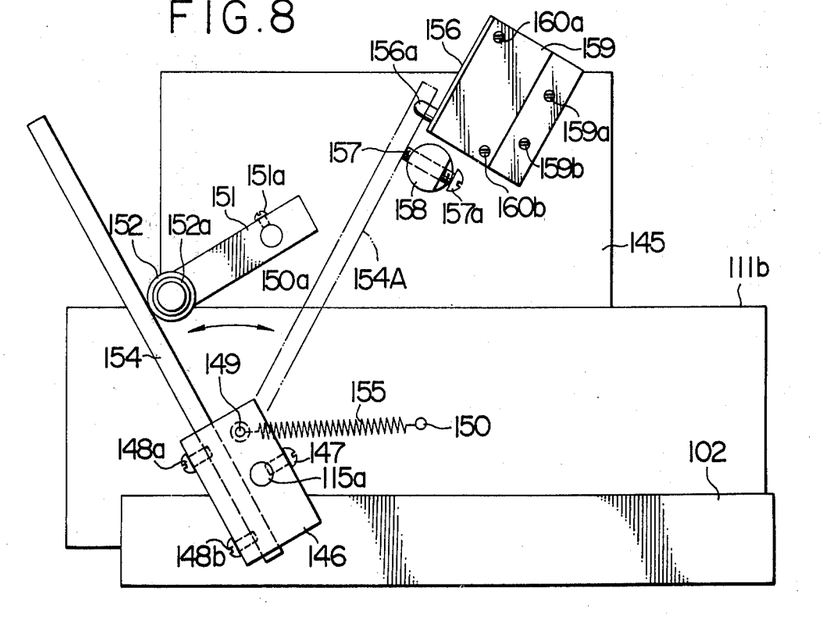
FIG. 8 is a side elevation of part of the apparatus shown in FIG. 5.

In addition to the continuous feed motor 125, an intermittent feed motor 150 is fixedly mounted on the top 111c of the roller support box 111 by means of a mounting plate 145, as shown in FIG. 7. The motor 150 has an output shaft 150a on which one end of an arm member 151 is fitted and secured thereto by a set screw 151a. The free end of the arm member 151 carries a pressure roller 152 which is pivotally mounted at 152a. A mounting member 146 is fitted on the right-hand end, as viewed in FIG. 7, of the shaft 115a associated with the feed roller 115, and is integrally secured thereto by a set screw 147 (see FIG. 8). A rocking arm 154 is fitted into the mounting member 146 and is integrally secured thereto by a pair of set screws 148a, 148b. It is to be noted that the feed roller 115 and the shaft 115a are interconnected by a one way rotational clutch, not shown, such that the connection therebetween is only effective in a direction to feed the specimen film 110 to the right, as viewed in FIG. 5.

The free end of the rocking arm 154 is located on a path of rotation of the roller 152 carried by the arm member 151, and is normally biased by a spring 155 (see FIG. 8), extending between a pin 149 fixedly mounted on the mounting member 146 and another pin 150 mounted on one wall 111b of the roller support box 111, into a position 154A shown in phantom line, in which it bears against a stop 157, thus pressing against the actuator 156a of a microswitch 156. The stop 157 threadably engages a support rod 158 which is fixedly mounted on the mounting plate 145 of the motor 150, and the position at which it bears against the rocking arm 154 can be adjusted by turning its head 157a. The microswitch 156 is secured to a support plate 159 by a pair of set screws 160a, 160b, which support plate 159 is secured to the mounting plate 145 by means of a pair of set screws 159a, 159b.

In operation, the specimen film 110 which is dyed, decolorized and dried is loaded into the apparatus 101 from the left-hand side, as viewed in FIG. 5, and the continuous feed motor 125 is set in motion, whereby the four pairs of feed rollers 113, 114; 115, 116; 117, 118; 119, 120 are simultaneously driven to rotate through the chain 128. The rotation of these rollers is effective to feed the specimen film 110 from left to right, as viewed in FIG. 5. During such movement, when the film 110 passes betweeen the rollers 115 and 116, the clearing liquid 103a is applied to the film 110 by the roller 116 which is partially immersed into such liquid, whereby the film 110 is uniformly made clear. The application of the clearing liquid to the film can be assured by using a hygroscopic material such as sponge for the roller 116. As the film 110 is fed further to the right, it is fed into the space between the pair of transparent glass plates 104a, 104b, moving therethrough. When the leading end of the film reaches a position between the light emitting diode 135b and the transducer element 135a, there occurs a change in the amount of light reaching the latter, whereby a signal is produced to interrupt the operation of the continuous feed motor 125, holding the film at the position which it then occupies. Since the film 110 is made clear by the liquid 103a by this time, the change in the amount of light may be reduced, making the detection difficult. To overcome this difficulty, it is desirable that the leading portion of the film 110 be provided with an opaque position mark. When the film 110 is stopped at a given position in this manner, the scan motor 143 is set in motion, whereby the pinion 144 and the rack 142 causes the box 130 supporting the light source unit, which has its exit pupil 134a positioned laterally of the specimen film 110 initially, to be displaced at the measuring port C in a direction to tranverse the film 110, or in the vertical direction as viewed in FIG. 6. As the box 130 is displaced in this manner, the support plate 137a for the transducer element 136 is also moved integrally therewith. As a result, the specimen film 110 is scanned by an illuminating light emanating from the lamp 131 while remaining at the given position, and the light transmitted through the foremost specimen is received by the transducer element 136 for utilization by a measuring device, not shown. The position of the transducer element 135a and the light emitting diode 135b as well as the exit pupil 134a in the box 130 is chosen in correct alignment with the pitch p of the specimens on the film 110 so that the fractionated pattern of the foremost specimen is aligned with the optical path of the illuminating light, thus assuring an accurate scanning of the fractionated pattern. The fractionated pattern of the specimen as detected by the transducer element 136 is recorded by a suitable recorder, not shown. When the determination of one fractionated pattern of the blood serum is completed, the scan motor 143 is driven in the opposite direction as by a suitably located limit switch, thereby returning the box 130 and the transducer element 136 to their original positions. At the same time, the intermittent feed motor 150 is set in motion, whereby the arm member 151 is rotated to drive the feed roller 115 and hence the four pairs of feed rollers which are operationally connected therewith through the chain 128 by a given increment. In this manner, the film 110 is fed by one pitch, whereby the fractionated pattern of a second specimen is located at the measuring port C. Thereupon, the scan motor 143 is again set in motion for determination of the density of the fractionated pattern of the second specimen. In this manner, the fractionated pattern of individual specimens applied to the film 110 as successively determined and when the determination has been completed for all of the specimens, the continuous feed motor 125 is again set in motion to deliver the film 110 externally of the apparatus 101. Any amount of clearing liquid 103b which may drip from the film during the measurement or during the feeding operation, for example, during its passage between the rollers 117, 118, is received in the recess 102b of the liquid vessel 102.

What is claimed is:

1. An apparatus for automatic quantitative analysis of specimens by cataphoretic process comprising a supply of clearing liquid which is to be supplied to a specimen film carrying a plurality of specimens disposed at a given pitch thereon; light source means for projecting a measuring light onto the specimen film which has been made clear by treatment with the clearing liquid; a measuring device including a photoelectric transducer element which receives light transmitted through the specimen film; a measuring port associated with a feed path of the specimen film and located intermediate the light source means and the photoelectric transducer element; intermittent feed means for intermittently feeding the specimen film by an increment corresponding to the pitch of the specimens on the film so as to sequentially advance each of the specimens to the measuring port one at a time; and scan drive means for displacing the light source means and the transducer means crosswise of the specimen film at the measuring port at each end of the incremental movement of the specimen film, thereby scanning the specimen located at the measuring port.

2. An apparatus according to claim 1 in which the supply of clearing liquid includes a vessel for receiving a quantity of clearing liquid, the feed path of the specimen film extending through the vessel, whereby the specimen film is immersed into the clearing liquid while it is being fed through the vessel.

3. An apparatus according to claim 2 in which the vessel comprises a transparent material, and the light source means and the transducer element are disposed on the opposite sides of the transparent vessel to define the measuring port, whereby the transducer element receives light transmitted through the transparent vessel and the specimen film located therein.

4. An apparatus according to claim 2 in which the vessel comprises a transparent material, the light source means and the transducer element being disposed on one side of the transparent vessel, further including a reflecting mirror on the opposite side of the transparent vessel to define the measuring port, whereby light emanating from the light source means transmits through the transparent vessel and the specimen film located therein, and is then reflected by the reflecting mirror to transmit through the transparent vessel and the specimen film located therein again to be received by the transducer element.

5. An apparatus according to claim 4, further including a light path conversion member located between the light source means and the transducer element for providing an optical separation therebetween.

6. An apparatus according to claim 5 in which the light path conversion member comprises a half mirror.

7. An apparatus according to claim 2, further including a pair of applicator rollers, at least one of which is immersed in the clearing liquid contained in the vessel, whereby the clearing liquid is applied to the specimen film as it is being fed by the pair of rollers.

8. An apparatus according to claim 7 in which the light source means and the transducer element are disposed on the opposite sides of the feed path of the specimen film at a position beyond the supply of clearing liquid so as to define the measuring port where the transducer element receives light emanating from the light source means and which has transmitted through the specimen film.

9. An apparatus according to claim 8, further including a pair of transparent plates located at the measuring port for holding the specimen film therebetween.

* * * * *